United States Patent
Koski

(10) Patent No.: US 6,310,230 B1
(45) Date of Patent: Oct. 30, 2001

(54) N-SUBSTITUTED-OMEGA-(ALKOXYSILYL) ALKYLAMINES AND PROCESS FOR PRODUCTION THEREOF

(75) Inventor: Ahti August Koski, Wilkesport (CA)

(73) Assignee: Bayer Inc., Sarnia (CA)

( * ) Notice: Subject to any disclaimer, the term of this patent is extended or adjusted under 35 U.S.C. 154(b) by 0 days.

(21) Appl. No.: 09/424,213

(22) PCT Filed: May 21, 1998

(86) PCT No.: PCT/CA98/00500

§ 371 Date: Nov. 19, 1999

§ 102(e) Date: Nov. 19, 1999

(87) PCT Pub. No.: WO98/52954

PCT Pub. Date: Nov. 26, 1998

(30) Foreign Application Priority Data

May 22, 1997 (CA) ................................................ 2205790

(51) Int. Cl.⁷ ...................................................... C07F 7/10
(52) U.S. Cl. ........................... 556/413; 427/216; 427/220
(58) Field of Search ............................. 556/413; 427/216, 427/220

(56) References Cited

FOREIGN PATENT DOCUMENTS

1955023 * 5/1970 (DE).

OTHER PUBLICATIONS

Yamaguchi et al., "Chemical Abstracts", vol. 117, No. 24, p. 244151, Dec. 1992.*
Suzuki, "Chemical Abstracts", vol. 126, No. 13, p. 172736, Mar. 1997.*
Kuwahara et al., "Chemical Abstracts", vol. 104, No. 22, p. 196864, Jun. 1986.*

E.J. Sadler, Plastics, Rubber and Composites Processing and Applications, vol. 24, No. 5, (month unavailable) 1955, pp. 271–275, Silane treatment of mineral fillers—practical aspects.

* cited by examiner

Primary Examiner—Paul F. Shaver
(74) Attorney, Agent, or Firm—Joseph C. Gil; Noland J. Cheung

(57) ABSTRACT

N-substituted-ω-(alkoxysilanes) of formula (I)

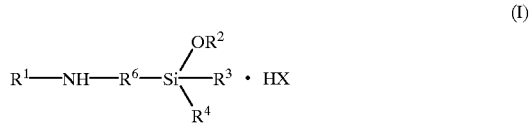

wherein:

$R^1$ is a $C_{12}$–$C_{30}$ alkyl or alkenyl group that is straight-chained or branched, a $C_5$–$C_{40}$ aryl group, a $C_5$–$C_{40}$ aralkyl group or a group $R_5A(CH_2)_p$ wherein $R_5$ is a $C_6$–$C_{30}$ alkyl or alkenyl group that is straight-chained or branched, p is an integer from 2 to 6 and A is O or NH; $R^2$ is a $C_1$–$C_{12}$ alkyl group (preferably a $C_1$–$C_5$ alkyl group) or a $C_3$–$C_{12}$ alkenyl group (preferably a $C_3$–$C_5$ alkenyl group); $R^3$ is a $C_1$–$C_{12}$ alkyl group (preferably a $C_1$–$C_5$ alkyl group), a $C_1$–$C_{12}$ alkoxy group (preferably A $C_1$–$C_5$ alkoxy group), a $C_2$–$C_{12}$ alkenyl group (preferably a $C_2$–$C_5$ alkenyl group) or a $C_3$–$C_{12}$ alkenyloxy group (preferably a $C_3$–$C_5$ alkenyloxy group); $R^4$ has the same definition as $R^3$ and may be the same as $R^4$ or different; $R^6$ is a divalent alkylene group having up to 10 carbon atoms and is optionally interrupted one, two or three times by a phenylene group; and X is an anion; and its free base are disclosed, and processes for their preparation. These compounds are useful for treatment of mineral particles, to alter the surface properties of the particles.

42 Claims, No Drawings

N-SUBSTITUTED-OMEGA-(ALKOXYSILYL) ALKYLAMINES AND PROCESS FOR PRODUCTION THEREOF

TECHNICAL FIELD

The present invention relates to N-substituted-ω-(alkoxysilyl)alkylamines and salts thereof, and to a process for production thereof.

BACKGROUND ART

Certain silane compounds, including some amine-containing silane compounds, are said to be useful for attaching organic groups to mineral fillers; see "Silane treatment of mineral fillers—practical aspects", by E. J. Sadler, Plastics, Rubber and Composites Processing and Applications Vol. 24, No. 5, 1995, pages 271 to 275.

It is known to prepare some N-substituted-3-(trialkoxysilyl)propylamines by reacting a 3-chloropropyltrialkoxysilane with a primary amine or reacting an alkyl chloride with a 3-aminopropyltrialkoxysilane, at reflux in an alcoholic solution, where the alcohol solvent corresponds to the alkyl group of the alkoxy portion of the silane. This is largely unsatisfactory as the alcohols $CH_3OH$, $C_2H_5OH$ and $C_3H_7OH$ boil at temperatures below 98° C., which is lower than the temperature required to obtain good yields of the desired products in a reasonable time. While higher boiling alcohols, for example butanol, may be used to achieve higher reflux temperatures and hence increased reaction rates, this can result in an exchange of alkoxy groups of the alcohol with those of the silane and a much decreased yield of the desired product The reaction rates can be increased by using higher temperatures and a pressure autoclave, but this still requires removal of the solvent alcohol, which complicates the synthesis, and also requires specialized equipment (autoclave), which is undesirable.

It is also known to prepare some N-substituted-3-(trialkoxysilyl)propylamines by reacting 3-bromopropyltrialkoxysilane with a primary amine, or reacting an alkyl bromide with a 3-aminopropyltrialkoxysilane at reflux in alcohol solution. Again, it is desirable that the alkoxy group of the alcohol is the same as the alkoxy group of the silane. While in some cases satisfactory yields can be obtained, in others the temperature of the boiling solvent is too high, causing unwanted side reactions, for instance dehydrobromination of the starting 3-bromopropyltrialkoxysilane. In any case, it is necessary to remove the alcohol to obtain the required product, which is expensive and disadvantageous, particularly if it is important to remove all traces of the solvents.

SUMMARY OF THE INVENTION

It is an object of the present invention to obviate or mitigate at least one of the above-identified disadvantages of the prior art.

It is another object of the present invention to provide novel N-substituted-ω-(alkoxysilyl)alkylamines and salts thereof.

It is yet another object of the present invention to provide a novel process for producing N-substituted-ω-(alkoxysilyl)alkylamines and salts thereof.

Accordingly, in one of its aspects, the present invention provides a process for producing a compound of Formula I:

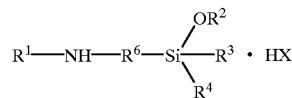

(I)

wherein $R^1$ is a $C_6$–$C_{40}$ alkyl or alkenyl group that is straight-chained or branched, a $C_6$–$C_{40}$ aryl group, a $C_7$–$C_{40}$ aralkyl group or a group $R_5A(CH_2)_p$ wherein $R_5$ is a $C_6$–$C_{30}$ alkyl or alkenyl group that is straight-chained or branched, p is an integer from 2 to 6 and A is O or NH;

$R^2$ is a $C_1$–$C_{12}$ alkyl group (preferably a $C_1$–$C_5$ alkyl group) or a $C_3$–$C_{12}$ alkenyl group (preferably a $C_3$–$C_5$ alkenyl group);

$R^3$ is a $C_1$–$C_{12}$ alkyl group (preferably a $C_1$–$C_5$ alkyl group), a $C_1$–$C_{12}$ alkoxy group (preferably a $C_1$–$C_5$ alkoxy group), a $C_2$–$C_{12}$ alkenyl group (preferably a $C_2$–$C_5$ alkenyl group) or a $C_3$–$C_{12}$ alkenyloxy group (preferably a $C_3$–$C_5$ alkenyloxy group);

$R^4$ has the same definition as $R^3$ and may be the same as $R^4$ or different;

$R^5$ is a divalent alkylene group having up to 10 carbon atoms and is optionally interrupted one, two or three times by a phenylene group; and X is an anion;

the process comprising the step of:

(a) reacting a compound of the Formula II:

(II)

wherein $R^1$ is as defined above, with a compound of Formula III:

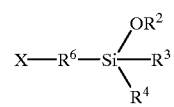

(III)

wherein $R^2$, $R^3$, $R^4$, $R^6$ and X are as defined above, in the absence of a solvent; or (b) reacting a compound of the Formula IV:

(IV)

wherein $R^1$ and X are as defined above, with a compound of Formula V:

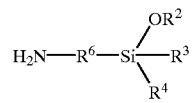

(V)

wherein $R^2$, $R^3$, $R^4$ and $R^6$ are as defined above, in the absence of a solvent.

It is surprising that the N-substituted-ω-(alkoxysilyl) alkylamines of Formula I can be obtained in good yields, within reasonable reaction times, without contamination by alcoholic solvent and without necessity for removal of alcoholic solvent.

In another of its aspects, the present invention provides a compound of Formula I:

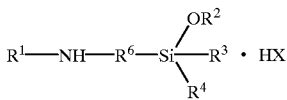

(I)

wherein
$R^1$ is a $C_{12}$–$C_{40}$ alkyl or alkenyl group that is straight-chained or branched, a $C_6$–$C_{40}$ aryl group, a $C_7$–$C_{40}$ aralkyl group or a group $R_5A(CH_2)_p$ wherein $R_5$ is a $C_6$–$C_{30}$ alkyl or alkenyl group that is straight-chained or branched, p is an integer from 2 to 6 and A is O or NH;

$R^2$ is a $C_1$–$C_{12}$ alkyl group (preferably a $C_1$–$C_5$ alkyl group) or a $C_3$–$C_{12}$ alkenyl group (preferably a $C_3$–$C_5$ alkenyl group);

$R^3$ is a $C_1$–$C_{12}$ alkyl group (preferably a $C_1$–$C_5$ alkyl group), a $C_1$–$C_{12}$ alkoxy group (preferably a $C_1$–$C_5$ alkoxy group), a $C_2$–$C_{12}$ alkenyl group (preferably a $C_2$–$C_5$ alkenyl group) or a $C_3$–$C_{12}$ alkenyloxy group (preferably a $C_3$–$C_5$ alkenyloxy group);

$R^4$ has the same definition as $R^3$ and may be the same as $R^4$ or different;

$R^6$ is a divalent alkylene group having up to 10 carbon atoms and is optionally interrupted one, two or three times by a phenylene group; and X is an anion.

In another of its aspects, the present invention provides a compound of Formula:

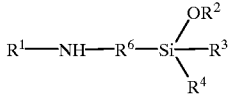

wherein
$R^1$ is a $C_{12}$–$C_{40}$ alkyl or alkenyl group that is straight-chained or branched, a $C_6$–$C_{40}$ aryl group, a $C_7$–$C_{40}$ aralkyl group or a group $R_5A(CH_2)_p$ wherein $R_5$ is a $C_6$–$C_{30}$ alkyl or alkenyl group that is straight-chained or branched, p is an integer from 2 to 6 and A is O or NH;

$R^2$ is a $C_1$–$C_{12}$ alkyl group (preferably a $C_1$–$C_5$ alkyl group) or a $C_3$–$C_{12}$ alkenyl group (preferably a $C_3$–$C_5$ alkenyl group);

$R^3$ is a $C_1$–$C_{12}$ alkyl group (preferably a $C_1$–$C_5$ alkyl group), a $C_1$–$C_{12}$ alkoxy group (preferably a $C_1$–$C_5$ alkoxy group), a $C_2$–$C_{12}$ alkenyl group (preferably a $C_2$–$C_5$ alkenyl group) or a $C_3$–$C_{12}$ alkenyloxy group (preferably a $C_3$–$C_5$ alkenyloxy group);

$R^4$ has the same definition as $R^3$ and may be the same as $R^4$ or different; and $R^6$ is a divalent alkylene group having up to 10 carbon atoms and is optionally interrupted one, two or three times by a phenylene group.

DESCRIPTION OF THE PREFERRED EMBODIMENTS

The anion X is suitably a chloride, bromide or iodide anion, of which the chloride and the bromide are preferred. The preferred reaction conditions vary, depending upon whether X is chlorine or bromine. If X is chlorine, it is preferred to carry out the reaction at a temperature at least about 100° C., more preferably in the range of from about 130° C. to about 185° C. The reaction may take anywhere from about 30 minutes to about 4 hours. If X is bromine, then it is preferred to operate at a lower temperature, preferably from about 30° C. to about 75° C. With bromine the reaction proceeds more slowly and reaction times of from about 8 to 24 hours are not unusual.

In one embodiment of the present process, an amine compound of Formula II is reacted with an alkoxysilane compound of Formula Ill.

Non-limiting examples of suitable amines of Formula II may be selected from the group comprising hexylamine, octylamine, nonylamine, decylamine, octadecylamine, octadec-enylamine and mixtures thereof. Indeed, mixed amines are commercially available and these are conveniently suitable for use. Nonimited examples of such amines may be selected from the group comprising soya amine, tall oil amine, stearyl amine, tallow amine, dihydrogenated tallow amine, cocoamine, rosin amine, palmitylamine and mixtures thereof. These amines may be use in distilled or undistilled form. When $R^1$ is alkenyl, it may contain one, two or more doublebonds and when it contains two or more double bonds, they may be conjugated or unconjugated.

In another embodiment of the present process, an amine compound of Formula IV is reacted with an alkoxysilane compound of Formula V.

Non-limiting examples of suitable alkyl or alkenyl halides of Formula IV may be selected from the group comprising 1-bromooctane, 1-chlorononane, 1-bromononane, 1-bromodecane, 1-chlorododecane, 1-bromooctadecane, 1-bromooctadec-9-ene and mixtures thereof. Indeed, mixed alkyl/alkenyl halides are commercially available and these are conveniently suitable for use. Nonlimited examples of such alkyualkenyl halides may be selected from the stearyl chloride, stearyl bromide, oleyl chloride and mixtures thereof. These materials may be use in distilled or undistilled form. Again, $R^1$ is alkenyl, it may contain one, two or more double bonds and when it contains two or more double bonds, they may be conjugated or unconjugated.

In the compound of Formula III or V, as stated $R^2$ is preferably $C_1$–$C_5$ alkyl or $C_3$–$C_5$ alkenyl, but more preferably it is $C_1$–$C_3$ alkyl, i.e., methyl, ethyl, propyl or isopropyl. It is preferred that $R^3$ and $R^4$ are $C_1$–$C_5$ alkoxy, particularly methoxy, ethoxy, propoxy or isopropoxy. It is preferred that $OR^2$, $R^3$ and $R^4$ are all the same and are methoxy. If $OR^2$, $R^3$ and $R^4$ are not the same it is preferred that $R^3$ and $R^4$ are alkyl or alkenyl. Preferably $R^2$, $R^3$ and $R^4$ are unsubstituted, but the use of substituted groups is not excluded, provided that the substituent does not interfere with the course of the reaction. These remarks also apply in respect of $R^1$ and $R^6$.

The reactions may be carried out under inert atmosphere, for example by flushing the reactor with an inert gas such as argon or nitrogen. This is not essential, however.

The reaction of the compound of Formula II with the compound of Formula III, or the compound of Formula IV with the compound of Formula V, results in release of the acid HX. Generally, the product of reaction will therefore be in the form of its acid addition salt with HX. For many purposes the compounds of Formula I can be used in the form of their salts. Alternatively, they can be converted from the salt to the free base, if needed. This is best done by reacting the compound with an alkali metal alkoxide in which the alkyl moiety is $R^2$, as defined above. For instance, if $R^2$ is methyl, it is preferred to use sodium methoxide to convert the salt to the free base.

Particularly, if the compounds of Formula I are to be used to render a material hydrophobic, it is preferred that $R^1$ is a longer chain alkyl or alkenyl group that preferably has ten carbon atoms, more preferably twelve carbon atoms, and more, and it is preferred that the chain is not branched at the atom connecting $R^1$ to the nitrogen.

It is believed that compounds of Formula I, prepared from mixed amines of more than 12 carbon atoms are novel. Thus, these compounds, in the acid addition salt form or free base form, are another aspect of the invention.

The compounds of Formula I are useful for treating mineral fillers to alter the properties of the mineral fillers. They can be used, for example, to treat silica, silicate mineral powders, clays, calcium carbonate, pigments such as titanium dioxide and other materials to render their surfaces hydrophobic. They can also be used as intermediates in the preparation of silica-bound catalysts and intermediates or ion-exchangers, or as coupling agents to improve the bond between paint and a wood or metal substrate, or as a waterproofing agent for wood or concrete.

Embodiments of the invention will be illustrated with reference to the following Examples which should to be used to construe or limit the scope of the invention.

EXAMPLE 1

Oleyl amine:(3-chloropropyl)trimethoxysilane 1:1 Adduct N-Oleyl-N-(3-trimethoxysilyl)propylamine ($R^1$=oleyl)

To a 1000 ml Erlenmeyer flask were added 267.5 grams of distilled oleylamine (Witco Kemamine 989D) and 198.8 grams of (3-chloropropyl)trimethoxysilane (Aldrich). A magnetic stirring bar and thermometer were inserted and the headspace above the liquid was flushed with Argon gas. The neck of the flask was then loosely plugged with tissue to hold the thermometer in place. The flask was placed on a hot plate and slowly heated to 160° C. over a period of 90 minutes with stirring. On cooling, the title compound, in the form of a yellow waxy solid (464.2 grams, m.p. 68–74° C.) was obtained. The material was readily soluble in methanol.

EXAMPLE 2

Palmityl amine:(3-chlorpropyl)trimethoxysilane 1:1 Adduct N-Palmity-N-(3-trimethoxsilyl)propylamine (R=palmityl)

To a 250 ml Erlenmeyer flask were added 60.5 grams of distilled palmitylamine (Akzo-Nobel Armeen 16D) and 50.4 grams of (3-chloropropyl)trimethoxysilane (Aldrich). A magnetic stirring bar and thermometer were inserted and the headspace above the slurry was flushed with Argon gas. The neck of the flask was then loosely plugged with tissue to hold the thermometer in place. The flask was placed on a hot plate and slowly heated with stirring to 50° C. to dissolve the amine. The heat was then increased and the contents were heated to 170° C. over a period of 30 minutes with stirring and then held at that temperature for 10 minutes. The heat was turned off and the flask was allowed to cool to room temperature over a one hour period. At 110° C., a yellow solid began to separate. The final yield was 107.1 grams of the title compound in the form of a yellow waxy solid (m.p. 106–110° C.) which dissolved readily in methanol.

EXAMPLE 3

Stearyl amine:(3chloropropyl)trimethoxysilane 1:1 Adduct N-Stearyl-N-(3-trimethoxysilyl)propylamine ($R^1$=stearyl)

To a 250 ml Erlenmeyer flask were added 76.7 grams of distilled stearylamine (Akzo-Nobel Armeen 18D) and 57.4 grams of (3-chloropropyl)trimethoxysilane (Aldrich). A magnetic stirring bar and thermometer were inserted. The neck of the flask was loosely plugged with tissue to hold the thermometer in place. The flask was placed on a hot plate and heated rapidly with stirring to 198° C. at which point the heat was shut off. The reaction endothermic kept the temperature at 190° C. for 10 minutes after which the material cooled quickly to room temperature. At 130° C., a yellow. solid began to separate. The final yield was 131.4 grams of the title compound in the form of a yellow waxy solid (m.p. 120–135° C.), easily soluble in methanol.

EXAMPLE 4

Dodecyl amine:(3-chloropropyl)trimethoxysilane 1:1 Adduct N-Dodeoyl-N-(3-trimethoxysilyl)propylamine ($R^1$=dodecyl)

To a 250 ml Erlenmeyer flask were added 22.9 grams of dodecylamine (Aldrich) and 24.8 grams of (3-chloropropyl)trimethoxysilane (Aldrich). A magnetic stirring bar and thermometer were inserted. The neck of the flask was then loosely plugged with tissue to hold the thermometer in place. The flask was placed on a hot plate and heated slowly to 185° C. with stirring, at which point the heat was reduced and the contents kept at 175–180° C. for 20 minutes. The heat was then shut off and the flask contents were allowed to cool. Solidification of the contents to an off-white solid began at around 50° C. The final product (47.3 grams) dissolved quickly in methanol with gentle stirring.

EXAMPLE 5

C-18 Tertiary alkyl primary amine:(3-chloropropyl)trimethoxysilane 1:1 Adduct ($R^1$=C18 tertiary primary alkyl)

To a 1000 ml Erlenmeyer flask were added 162.5 grams of C-18 tertiary alkyl primary amine (Primeness AM-T, Roam and Has) and 100.4 grams of (3-chloropropyl)trimethoxysilane (Aldrich). A magnetic stirring bar and thermometer were inserted. The neck of the flask was then loosely plugged with tissue to hold the thermometer in place. The flask was placed on a hot plate and heated slowly over a period of 95 minutes to 180° C. with stirring, at which point the heat was shut off and the flask contents were allowed to cool. No solidification occurred. 258.9 grams of a viscous amber liquid were recovered. The liquid was miscible with methanol in all proportions.

EXAMPLE 6

Tallow amine:(3-chloropropyl)trimethoxysilane 1:1 Adduct N-Tallow-alkyl-N-(3-trimethylsilyl)propylamine ($R^1$=tallow alkyl)

To a 1000 ml Erlenmeyer flask were added 134 grams of distilled tallow amine (Armeen DT, Akzo-Nobel) and 100.4 grams of (3-chloropropyl)trimethoxysilane (Aldrich). A magnetic stirring bar and thermometer were inserted. The neck of the flask was then loosely plugged with tissue to hold the thermometer in place, a needle was inserted and the headspace was flushed with Argon to remove air. The flask was placed on a hot plate and heated over a period of one hour to 180° C. with stirring, at which point the heat was shut off. The heat of reaction continued to raise the temperature to 192° C. after which the material cooled to room temperature over one hour. Solidification of the contents began at 65° C. and the material was completely solid by 55°

C. The yield was 234 grams of a yellowish pasty solid. This material dissolved easily in methanol to give a clear solution.

EXAMPLE 7

Octyl amine:(3-chloropropyl)trimethoxysilane 1:1 Adduct N-Octyl-N-(3-trimethoxysilyl)propylamine ($R^1$=octyl)

To a 500 ml 2-neck round bottom flask equipped with a drying tube and magnetic stirrer were added 99.5 grams of octylamine (Aldrich) and 154.5 grams of (3-chloropropyl) trimethoxysilane (Aldrich). A thermometer was inserted through a side arm. The flask was placed in a mantle equipped with a Variac controller and the heat was energized. Over a period of 85 minutes, the temperature climbed to 190° C. and then fell to 180° C. within 25 minutes at which point the heat was shut off. Solidification of the contents began at 60° C. and the material was completely solid by 50° C. The yield was 253.6 grams of the title compound in the form of a yellow solid. This material dissolved readily in methanol to give a clear yellow solution.

EXAMPLE 8

Cocoamine:(3-chloropropyl)trimethoxysilane 1:1 Adduct ($R^1$=cocoa alkyl)

To a 500 ml Erlenmeyer flask were added 100 grams of distilled cocoamine (Armeen CD, Akzo-Nobel) and 100 grams of (3-chloropropyly)trimethoxysilane (Aldrich). A magnetic stirring bar and thermometer were inserted and the neck of the flask was then loosely plugged with tissue to hold the thermometer in place. The flask was placed on a hot plate and heated over a period of 45 minutes to 185° C. with stirring, at which point the heat was turned off. The heat of reaction continued to raise the temperature to 200° C. over 5 minutes after which it fell to 125° C. 20 minutes later. 198.4 grams of product were isolated. At room temperature, the material was a yellow waxy solid which dissolved easily in methanol on gentle shaking.

EXAMPLE 9

1-Chlorodecane:(3-aminopropyl)trimethoxysilane 1:1 Adduct N-Decyl-N-(3trimethoxyilyl) propylamine ($R^1$=decyl)

To a 500 ml Erlenmeyer flask were added 95 grams of 1-chlorodecane (Aldrich) and 96.4 grams of (3-aminopropyl)trimethoxysilane (Petrarch/UCT). A magnetic stirring bar and thermometer were inserted and the neck of the flask was then loosely plugged with tissue to hold the thermometer in place. The flask was placed on a hot plate and heated with stirring. After 90 minutes the temperature reached 184° C. and then fell to 175° C. 20 minutes later at which point the heat was turned off and the material removed from the hot plate. When cooled, the material was a waxy solid, and was recovered which dissolved easily in methanol.

EXAMPLE 10

1-Bromododecane:(3-aminopopyl)trimethoxysilane 1:1 Adduct N-Dodecyl-N-(3-trimethoxysilyl) propylamine ($R^1$=dodecyl)

To a 100 ml Erlenmeyer flask were added 24.9 grams of 1-bromododecane (Aldrich) and 17.9 grams of (3-aminopropyl)trimethoxysilane (Petrarch/UCT). The flask was stoppered and shaken to effect mixing. The material was allowed to stand undisturbed at room temperature (23° C.) for 5 hours. Examination of the mixture after this period revealed an upper phase consisting of a clear liquid and a lower phase of feathery white crystals. The flask was transferred to a hot plate previously equilibrated to give a surface temperature of 45 and left for 16 hours. At the end of this time all the material had reacted to give 41.2 grams of pale yellow crystals. An NMR spectrum was consistent with that expected from N-dodecyl-N-(3-trimethoxysilyl)propyl ammonium bromide. The material was freely soluble in methanol with a distinct endothermic effect.

EXAMPLE 11

Soya amine:(3-chloropropyl)trimethoxysilane 1:1 Adduct ($R^1$=soya-alkyl)

To a 1000 ml Erlenmeyer flask were added 263.6 grams of distilled soya amine (Ado-Nobel Armeen SD) and 198.7 grams of (3-chloropropyl)trimethoxysilane (Aldrich). A magnetic stirring bar and thermometer were inserted. The neck of the flask was loosely plugged with tissue to hold the thermometer in place. The flask was placed on a hot plate and heated slowly to 45 in order to effect solution of the soya amine. It was then heated to 160° C. over two hours and then held at 147–160° C. for a further two hours after which it was allowed to cool slowly to room temperature. Yellow crystals began to separate from the mother liquid at 75° C. and at room temperature the contents of the flask comprised a yellow solid mass. The yield was 460.0 grams. The product was easily soluble in methanol to give a clear yellowish solution.

What is claimed is:

1. A process for producing a compound of Formula I:

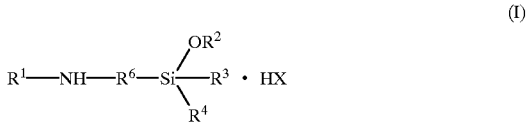

(I)

wherein
  $R^1$ is a $C_6$–$C_{40}$ alkyl or alkenyl group that is straight-chained or branched, a $C_6$–$C_{40}$ aryl group, a $C_7$–$C_{40}$ aralkyl group or a group $R_5A(CH_2)_p$ wherein $R_5$ is a $C_6$–$C_{30}$ alkyl or alkenyl group that is straight-chained or branched, p is an integer from 2 to 6 and A is O or NH;
  $R^2$ is a $C_1$–$C_{12}$ alkyl group or a $C_3$–$C_{12}$ alkenyl group;
  $R^3$ is a $C_1$–$C_{12}$ alkyl group, a $C_1$–$C_{12}$ alkoxy group, a $C_2$–$C_{12}$ alkenyl group or a $C_3$–$C_{12}$ alkenyloxy group;
  $R^4$ has the same definition as $R^3$ and may be the same as $R^4$ or different;
  $R^6$ is a divalent alkylene group having up to 10 carbon atoms and is optionally interrupted one, two or three times by a phenylene group; and
  X is an anion;
wherein said process comprises the step of:
  (a) reacting a compound of the Formula II:

(II)

wherein $R^1$ is as defined above, with a compound of Formula III:

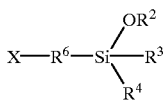
(III)

wherein $R^2$, $R^3$, $R^4$, $R^6$ and X are as defined above, in the absence of a solvent.

2. The process defined in claim 1, wherein, $R^2$ is a $C_1$–$C_5$ alkyl group.

3. The process defined in claim 1, wherein $R^2$ is a $C_3$–$C_5$ alkenyl group.

4. The process according to claim 1, wherein $R^3$ is a $C_1$–$C_5$ alkyl group.

5. The process according to claim 1, wherein $R^3$ is a $C_1$–$C_5$ alkoxy group.

6. The process according to claim 1, wherein $R^3$ is a $C_2$–$C_5$ alkenyl group.

7. The process according to claim 1, wherein $R^3$ is a $C_3$–$C_5$ alkenyloxy group.

8. The process according to claim 1, wherein X is chlorine.

9. The process defined in claim 8, wherein the reactants are heated to a temperature of at least about 100° C.

10. The process defined in claim 8, wherein the reactants are heated to a temperature in the range from about 130° to about 185° C.

11. The process according to claim 1, wherein X is bromine.

12. The process defined in claim 11, wherein the reactants are heated to temperature in the range from about 30° to about 50° C.

13. The process according to claim 1, wherein $R^6$ is the group —$(CH_2)_3$—.

14. The process according to claim 1, wherein $R^2$ is a $C_1$–$C_3$ alkyl group and $R^3$ and $R^4$ are each a $C_1$–$C_3$ alkoxy group.

15. The process according to claim 1, wherein $R^2$ is methyl and $R^3$ and $R^4$ are each a methoxy group.

16. The process according to claim 1, wherein $R^6$ is the group —$(CH_2)_3$—, $R^2$ is methyl and $R^3$ and $R^4$ are each a methoxy group.

17. The process according to claim 1, wherein the compound of Formula II is oleylamine.

18. The process according to claim 1, wherein the compound of Formula II is soya-amine.

19. The process according to claim 1, wherein the compound of Formula II is tall-oil-amine.

20. The process according to claim 1, wherein the compound of Formula III is (3-chloropropyl)trimethoxysilane.

21. A process for producing a compound of Formula I:

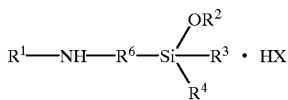
(I)

wherein
$R^1$ is a $C_6$–$C_{40}$ alkyl or alkenyl group that is straight-chained or branched, a $C_6$–$C_{40}$ aryl group, a $C_7$–$C_{40}$ aralkyl group or a group $R_5A(CH_2)_p$ wherein $R_5$ is a $C_6$–$C_{30}$ alkyl or alkenyl group that is straight-chained or branched, p is an integer from 2 to 6 and A is O or NH;

$R^2$ is a $C_1$–$C_{12}$ alkyl group or a $C_3$–$C_{12}$ alkenyl group;

$R^3$ is a $C_1$–$C_{12}$ alkyl group, a $C_1$–$C_{12}$ alkoxy group, a $C_2$–$C_{12}$ alkenyl group or a $C_3$–$C_{12}$ alkenyloxy group;

$R^4$ has the same definition as $R^3$ and may be the same as $R^4$ or different;

$R^6$ is a divalent alkylene group having up to 10 carbon atoms and is optionally interrupted one, two or three times by a phenylene group; and X is an anion;

wherein said process comprises the step of:

(a) reacting a compound of Formula IV:

$$R^1\text{—}X \qquad (IV)$$

wherein $R^1$ and X are as defined above with a compound of Formula V:

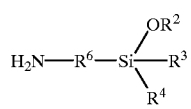
(V)

wherein $R^2$, $R^3$, $R^4$ and $R^6$ are as defined above, in the absence of a solvent.

22. The process according to claim 21, wherein $R^2$ is a $C_1$–$C_5$ alkyl group.

23. The process according to claim 21, wherein $R^2$ is a $C_3$–$C_5$ alkenyl group.

24. The process according to claim 21, wherein $R^3$ is a $C_1$–$C_5$ alkyl group.

25. The process according to claim 21, wherein $R^3$ is a $C_1$–$C_5$ alkoxy group.

26. The process according to claim 21, wherein $R^3$ is a $C_2$–$C_5$ alkenyl group.

27. The process according to claim 21, wherein $R^3$ is a $C_3$–$C_5$ alkenyloxy group.

28. The process according to claim 21, wherein X is chlorine.

29. The process according to claim 21, wherein the reactants are heated to a temperature of at least about 100° C.

30. The process according to claim 29, wherein the reactants are heated to a temperature in the range from about 130° C. to about 185° C.

31. The process according to claim 21, wherein X is bromine.

32. The process according to claim 21, wherein the reactants are heated to a temperature in the range from about 30° C. to about 50° C.

33. The process according to claim 21, wherein $R^6$ is the group —$(CH_2)_3$—.

34. The process according to claim 21, wherein $R^2$ is a $C_1$–$C_3$ alkyl group and $R^3$ and $R^4$ are each a $C_1$–$C_3$ alkoxy group.

35. The process according to claim 21, wherein $R^2$ is methyl and $R^3$ and $R^4$ are each a methoxy group.

36. The process according to claim 21, wherein $R^6$ is the group —$(CH_2)_3$—, $R^2$ is methyl and $R^3$ and $R^4$ are each a methoxy group.

37. A process for hydrophobicizing particles for use as filler in a polymer masterbatch comprising treating said particles with compound of formula I:

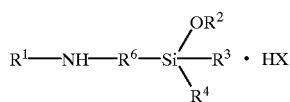

wherein
- $R^1$ is a $C_6$–$C_{40}$ alkyl or alkenyl group that is straight-chained or branched, a $C_6$–$C_{40}$ aryl group, a $C_7$–$C_{40}$ aralkyl group or a group $R_5A(CH_2)_p$ wherein $R_5$ is a $C_6$–$C_3$ alkyl or alkenyl group that is straight-chained or branched, p is an integer from 2 to 6 and A is O or NH;
- $R^2$ is a $C_1$–$C_{12}$ alkyl group or a $C_3$–$C_{12}$ alkenyl group;
- $R^3$ is a $C_1$–$C_{12}$ alkyl group, a $C_1$–$C_{12}$ alkoxy group, a $C_2$–$C_{12}$ alkenyl group or a $C_3$–$C_{12}$ alkenyloxy group;
- $R^4$ has the same definition as $R^3$ and may be the same as $R^4$ or different;
- $R^6$ is a divalent alkylene group having up to 10 carbon atoms and is optionally interrupted one, two or three times by a phenylene group; and
- X is an anion.

38. A process for hydrophobicizing particles for use as filler in a rubber vulcanizate comprising treating said particles with compound of formula I:

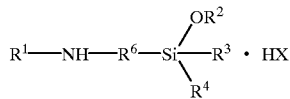

wherein
- $R^1$ is a $C_6$–$C_{40}$ alkyl or alkenyl group that is straight-chained or branched, a $C_6$–$C_{40}$ aryl group, a $C_7$–$C_{40}$ aralkyl group or a group $R_5A(CH_2)_p$ wherein $R_5$ is a $C_6$–$C_{30}$ alkyl or alkenyl group that is straight-chained or branched, p is an integer from 2 to 6 and A is O or NH;
- $R^2$ is a $C_1$–$C_{12}$ alkyl group or a $C_3$–$C_{12}$ alkenyl group;
- $R^3$ is a $C_1$–$C_{12}$ alkyl group, a $C_1$–$C_{12}$ alkoxy group, a $C_2$–$C_{12}$ alkenyl group or a $C_3$–$C_{12}$ alkenyloxy group;
- $R^4$ has the same definition as $R^3$ and may be the same as $R^4$ or different;
- $R^6$ is a divalent alkylene group having up to 10 carbon atoms and is optionally interrupted one, two or three times by a phenylene group; and
- X is an anion.

39. A process according to claim 37, wherein said particles are hydrophilic mineral particles that have surface hydroxyl groups.

40. A process according to claim 38, wherein said particles are hydrophilic mineral particles that have surface hydroxyl groups.

41. A process according to claim 37, wherein said particles are selected from the group consisting of silica, silicates, clay, alumina and titanium dioxide.

42. A process according to claim 38, wherein said particles are selected from the group consisting of silica, silicates, clay, alumina and titanium dioxide.

* * * * *